United States Patent [19]

Suzuki et al.

[11] Patent Number: 5,346,935
[45] Date of Patent: Sep. 13, 1994

[54] HYDROGEL

[75] Inventors: Yasuyuki Suzuki, Suita; Hisayoshi Shimizu, Takatsuki, both of Japan

[73] Assignee: Takeda Chemical Industries, Ltd., Osaka, Japan

[21] Appl. No.: 144,510

[22] Filed: Nov. 2, 1993

Related U.S. Application Data

[63] Continuation of Ser. No. 888,926, May 27, 1992, abandoned.

[30] Foreign Application Priority Data

May 28, 1991 [JP] Japan ................................. 3-154000

[51] Int. Cl.$^5$ ................................................. C08L 1/00
[52] U.S. Cl. ......................................... 524/18; 524/17; 524/21; 524/24; 524/27; 524/29; 524/503; 524/557; 514/944; 424/486; 424/487; 424/488
[58] Field of Search ................ 524/27, 29, 503, 552, 524/17, 18, 21, 24

[56] References Cited

U.S. PATENT DOCUMENTS

| | | | |
|---|---|---|---|
| 4,012,352 | 3/1977 | Deyrup | 524/557 |
| 4,472,542 | 9/1984 | Nambu | 524/557 X |
| 4,582,865 | 4/1986 | Balazs et al. | 524/29 |
| 4,657,901 | 4/1987 | Ueda et al. | 514/171 |
| 4,663,358 | 5/1987 | Hyon et al. | 521/64 |
| 4,689,079 | 8/1987 | Buma et al. | 523/109 |
| 4,734,097 | 3/1988 | Tanabe et al. | 524/557 X |
| 4,774,957 | 10/1988 | Nambu et al. | 524/557 X |
| 4,916,170 | 4/1990 | Nambu et al. | 524/557 X |
| 5,141,973 | 8/1992 | Kobayashi et al. | 524/503 X |

FOREIGN PATENT DOCUMENTS

| | | |
|---|---|---|
| 0095892 | 12/1983 | European Pat. Off. . |
| 0107055 | 5/1984 | European Pat. Off. . |
| 0216362 | 4/1987 | European Pat. Off. . |
| 0312208 | 4/1989 | European Pat. Off. . |
| 60-177066 | 9/1985 | Japan . |
| 61-191609 | 8/1986 | Japan . |
| 2-178332 | 7/1990 | Japan . |

*Primary Examiner*—Judy M. Reddick
*Attorney, Agent, or Firm*—Wenderoth, Lind & Ponack

[57] ABSTRACT

The hydrogel of the invention contains polyvinyl alcohol (a hydrogel support), and a high water-absorbent resin and/or a hydrophilic high molecular compound, which are capable of containing a large amount of water. The rate of evaporation of water from this hydrogel is slow. The hydrogel retains water for a long time and releases an active ingredient gradually. The hydrogel containing a pharmacologically active substance is useful as a pharmaceutical preparation.

8 Claims, 1 Drawing Sheet

HYDROGEL

This application is a continuation application of now abandoned application, Ser. No. 07/888,926, filed May 27, 1992.

FIELD OF THE INVENTION

The present invention relates to a hydrogel and a method of producing the same. The present invention further relates to a pharmaceutical gel preparation which comprises a pharmacological active substance dispersed in a hydrogel comprising polyvinyl alcohol and one or more components capable of containing large amount of water.

BACKGROUND OF THE INVENTION

A hydrogel is a gel which contains water by hydration. Such hydrogels have been known for years but recently as the interest in functional materials has increased, unique properties of hydrogels have attracted special interest. Hydrogels generally are sparingly irritating to the tissues and are superior in permeability to various substances. Hydrogels also show improved antithrombotic activity with increasing water contents. Hydrogels are, thus, considered to be very promising medical raw materials.

Those skilled in the art know high polymers capable of forming such hydrogels such as gelatin, carrageenin, alginic acid, 2-hydroxyethyl polymethacrylate, polyacrylamide, polyvinyl alcohol and so on. Hydrogels can be produced by a number of methods. For polyvinyl alcohol (hereinafter referred to sometimes as PVA) hydrogel as an example, when a concentrated aqueous solution of PVA is prepared and allowed to stand at a temperature below room temperature, it progressively gains viscosity and ultimately gives a gel.

However, the PVA gel prepared in this manner is not satisfactory in mechanical strength. Therefore, a method was proposed which comprises freezing a concentrated aqueous solution of PVA at a low temperature in a brief time and thawing it at room temperature (Japanese Patent Application Kokai No. 52296/1975). A method has also been proposed in which a crosslinked gel is produced using a crosslinking agent such as formaldehyde or by irradiation with γ-rays, for instance. The resulting hydrogels have definite mechanical strength and flexibility and can be used as medical materials such as vehicles for slow-release of drugs, carriers for immobilization of enzymes and microbial cells, thermal carriers for cold retention, and bases for controlled release of aromas and perfumes.

While the hydrogel generally has the above-mentioned beneficial properties, the gel tends to shrink with time as it releases the entrapped water. Therefore, the hydrogel has not only poor formulation stability but, when such a hydrogel preparation is applied to the skin, it elicits irritable responses owing to vaporization of entrapped water.

The present inventors have conducted an intensive investigation to overcome these disadvantages. As the result, it has been found that a hydrogel with a minimum of change in water content and an improved formulation stability can be obtained by incorporating a water-containing component capable of containing a large amount of water into a hydrogel. The present invention is predicated on this finding.

SUMMARY OF THE INVENTION

The present invention provides a hydrogel comprising polyvinyl alcohol and at least one substance capable of containing water wherein the substance is selected from the group consisting of a high water-absorbent resin and a hydrophilic high molecular compound. The present invention also provides a method of producing such a hydrogel. The invention further provides a pharmaceutical preparation utilizing such a hydrogel.

PVA provides a hydrogel, but such a hydrogel easily releases the entrapped water. It is essential for producing the novel hydrogel stably containing a large amount of water that a high water-absorbent resin and/or a hydrophilic high molecular compound (hereinafter these are referred to sometimes as water-containing component) are incorporated into such a PVA hydrogel.

DETAILED DESCRIPTION OF THE INVENTION

Figure 1:
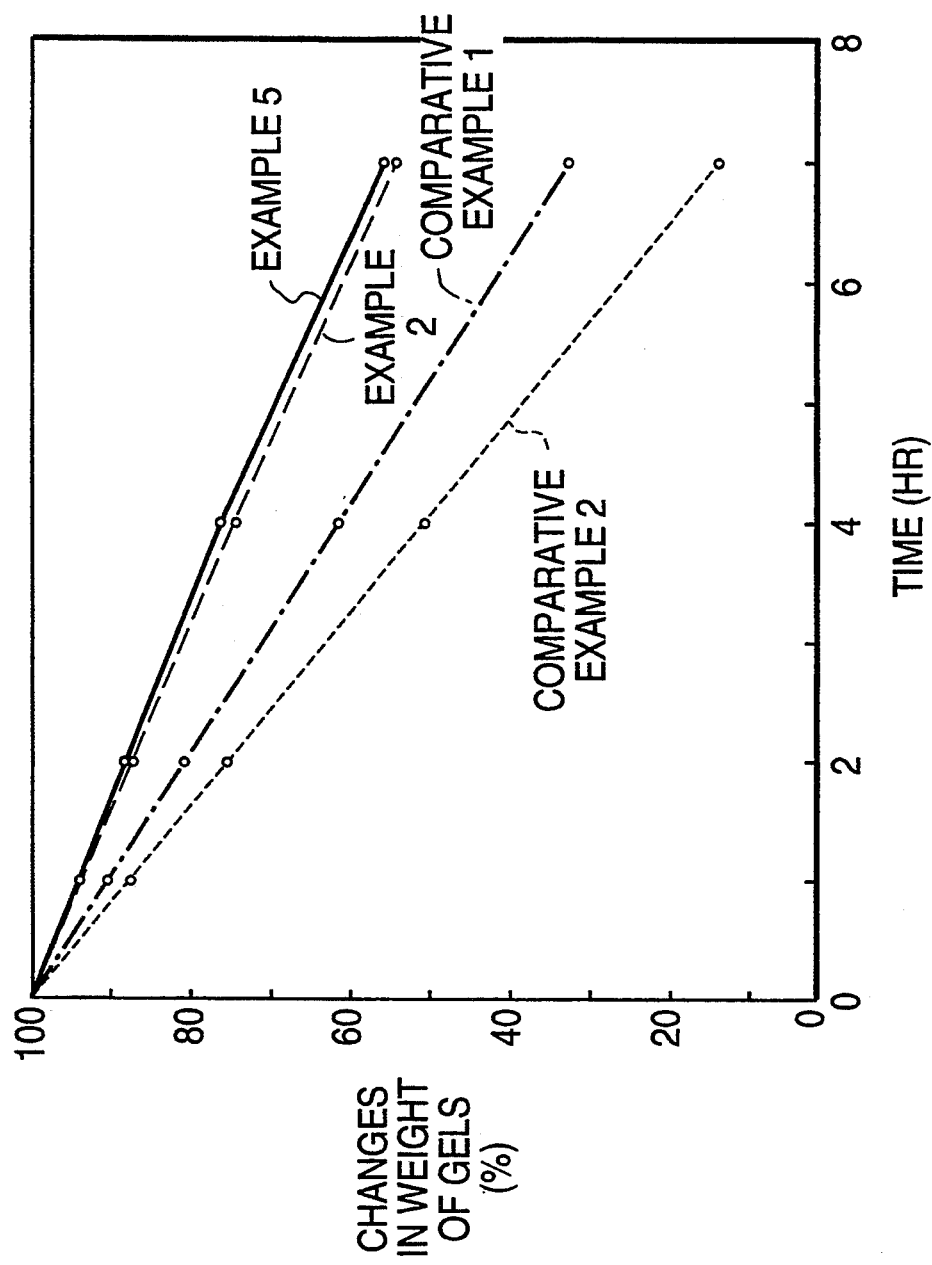
FIG. 1 is a graph showing changes in weight of hydrogels.

Polyvinyl alcohol is a high polymer which constitutes a support for a hydrogel of the present invention. The PVA used in the hydrogel of the invention preferably has an average degree of polymerization in the range of 1700 to 2500 and a saponification degree of not less than 95 mole percent.

On the other hand, the water-containing component is a resin or a high molecular compound capable of absorbing more than tens of times to more than one thousand times their weights of water, and holds water for a long term. Particularly preferred are resins and high molecular compounds, capable of absorbing about 50 to 2000 times their weights of water.

The high water-absorbent resin, one of the water-containing components, may be soluble in water or not soluble. The resin absorbs water to swell and hardly release water under the pressure. The resins include starch; celluloses such as methyl cellulose, carboxymethyl cellulose and the like; and a synthetic resin, which are resins composed of polyelectrolytes.

Specific examples of such synthetic resins include a metal salt of hydrolyzed copolymer composed of vinyl acetate and alkyl (meth)acrylate (e.g. a sodium salt of hydrolyzed copolymer composed of vinyl acetate and methyl acrylate: available from Sumitomo Chemical Company, Ltd. under the trade name of Sumikagel), crosslinked vinyl alcohol-maleic anhydride copolymer, crosslinked vinyl alcohol-acrylic acid-maleic anhydride copolymer, crosslinked isobutylene-maleic acid copolymer, saponified polyacrylonitrile graft polymer, starch-acrylic acid graft polymer and so on.

The another water-containing component, the hydrophilic high molecular compound used in the invention, is a compound which can dissolve in water, and holds a large amount of water by hydration. Such high molecular compounds have a dissociative group such as carboxyl group and/or hydrophilic group such as hydroxyl group. These compounds hardly release water under pressure.

Specific examples of such compounds include polyacrylate salt polymers, hyaluronic acid and its salts, β-1,3-glucan (Curdian: manufactured by Takeda Chemical Industries, Ltd.) and so on.

In the hydrogel of the invention, the amounts of such a high water-absorbent resin and hydrophilic high molecular compound are not critical. However, the total amount of these water-containing components is preferably about 0.1 to 10 weight %, more preferably about 0.5 to 2 weight %, based on the weight of the hydrogel, and is preferably about 1 to 25 parts by weight, more preferably about 2 to 10 parts by weight, to each 100 parts by weight of PVA.

Another high molecular compound may be incorporated into the hydrogel for adjusting the properties of the hydrogel, such as flexibility of the hydrogel. Such polymers which can be used in combination with PVA in this manner include, for example, gelatin, cartagechin, alginic acid, 2-hydroxyethyl polymethacrylate, carboxymethyl-starch, polyacrylamide, polyoxyethylene, polyvinylpyrrolidone, polystyrenesulfonic acid polymer and so on.

For producing a hydrogel from the above raw materials, polyvinyl alcohol and the water-containing components, a high water-absorbent resin and/or a hydrophilic high molecular compound, are mixed in water and heated to give an aqueous liquid. The aqueous liquid may be a homogeneous solution. When a water-insoluble high water-absorbent resin is used, the aqueous liquid may be partly a dispersion.

On dissolving the raw materials in water under heating, it is important to insure the uniformity of the aqueous liquid. The aqueous liquid thus obtained is then cooled to near room temperature to give a hydrogel. It is preferable that the aqueous liquid is frozen at about $-20°$ and, then, thawed by gradual warming to near room temperature. The latter procedure gives the desired hydrogel having a higher mechanical strength.

An active ingredient may be added during any steps mentioned above. However, if the active ingredient to be incorporated is a heat-labile substance, it is recommended to add the raw materials into water with heating and, after the aqueous liquid has cooled to near room temperature, add the active ingredient. The active ingredient which can be incorporated in the hydrogel includes peptides such as TRH (protirelin) and insulin, sulfa drugs, clonidine, steroid hormones, etc., although these are mere examples and not exclusive.

In the iontophoresis procedure where an active ingredient is to be delivered through the skin from a hydrogel by an electric potential, the active ingredient is not added on the reference electrode side. When an active ingredient is caused to be absorbed transdermally by iontophoresis, a hydrogel containing TRH and a hydrogel not containing TRH, for example, are prepared and applied to the skin and a current is passed for a predetermined time to cause absorption of the active substance.

EXAMPLES

The following examples are further illustrative of the present invention.

(Method of producing a hydrogel)

Polyvinyl alcohol and components capable of containing large amount of water were evenly mixed. The mixture was dispersed well by adding purified water portionwise at 60°–70° until a homogenous aqueous liquid is obtained. This aqueous liquid was poured in a casting mold and frozen at $-20°$ overnight. The frozen mass was then thawed at ambient temperature to give a hydrogel.

EXAMPLE 1

| Component | Amount |
| --- | --- |
| Polyvinyl alcohol (degree of polymerization 2000, degree of saponification 99%) | 5 g |
| Sodium hyaluronate | 0.5 g |
| TRH | 30 mg |
| Purified water to make | 100 g |

Using the above formula, a hydrogel was prepared by the method described hereinbefore.

EXAMPLE 2

| Component | Amount |
| --- | --- |
| Polyvinyl alcohol (degree of polymerization 2000, degree of saponification 99%) | 5 g |
| Sodium hyaluronate | 0.5 g |
| Purified water to make | 100 g |

Using the above formula, a hydrogel was prepared by the described method.

EXAMPLE 3

| Component | Amount |
| --- | --- |
| Polyvinyl alcohol (degree of polymerization 2000, degree of saponification 99%) | 4.5 g |
| Curdlan ($\beta$-1,3-glucan; manufactured by Takeda Chemical Industries, Ltd.) | 0.5 g |
| Ironate | 0.5 g |
| Sodium hyaluronate | 0.5 g |
| TRH | 30 mg |
| Sodium citrate | 50 mg |
| Purified water to make | 100 g |

Using the above formula, a hydrogel was prepared by the described method.

EXAMPLE 4

| Component | Amount |
| --- | --- |
| Polyvinyl alcohol (degree of polymerization 1700, degree oi saponification 95%) | 12 g |
| Polyvinyl alcohol (degree of polymerization 2500, degree of saponification 99%) | 0.5 g |
| Curdlan | 1.0 g |
| Sodium hyaluronate | 0.2 g |
| Dexamethasone | 5 mg |
| Purified water to make | 100 g |

Using the above formula, a hydrogel was prepared by the described method.

EXAMPLE 5

| Component | Amount |
| --- | --- |
| Polyvinyl alcohol (degree of polymerization 2000, degree of saponification 99%) | 5 g |
| Sumikagel SP 510 (a sodium salt of hydrolyzed copolymer composed of vinyl acetate and methyl acrylate; manufactured by Sumitomo Chemical Ltd.) | 0.5 g |
| TRH | 30 mg |

EXAMPLE 5-continued

| Component | Amount |
| --- | --- |
| Purified water to make | 100 g |

Using the above formula, a hydrogel was prepared by the described method.

COMPARATIVE EXAMPLE 1

| Component | Amount |
| --- | --- |
| Polyvinyl alcohol (degree of polymerization 2000, degree of saponification 99%) | 10 g |
| Purified water to make | 100 g |

Using the above formula, a hydrogel was prepared by the described method.

COMPARATIVE EXAMPLE 2

| Component | Amount |
| --- | --- |
| Polyvinyl alcohol (degree of polymerization 2000, degree of saponification 99%) | 5 g |
| Purified water to make | 100 g |

Using the above formula, a hydrogel was prepared by the described method.

The hydrogels prepared in Examples 2 and 5, and the hydrogels prepared Comparative Examples 1 and 2 were respectively put on a Petri dish and the evaporation amount of water from each gel was measured. For this measurement, each hydrogel was allowed to stand under open conditions in an incubator at 40° C. Because this was a comparative test, no provision was made for humidity control. The results are shown in Table 1 and FIG. 1.

TABLE 1

| Time (hr) | 0 | 1 | 2 | 4 | 7 |
| --- | --- | --- | --- | --- | --- |
| | \multicolumn{5}{c}{Change in weight (%)} |
| EXAMPLE 2 | 100 | 93.2 | 87.0 | 74.0 | 54.2 |
| EXAMPLE 5 | 100 | 93.5 | 88.3 | 76.4 | 56.6 |
| COMPARATIVE EXAMPLE 1 | 100 | 89.7 | 79.9 | 60.3 | 32.9 |
| COMPARATIVE EXAMPLE 2 | 100 | 86.5 | 74.2 | 48.4 | 13.9 |

It is apparent from Table 1 and FIG. 1 that whereas the weight loss was 70 to 80% in Comparative Examples 1 and 2, it was only about 40% in Examples 2 and 5.

The hydrogel of the invention is capable of retaining water for a long time and releasing an active ingredient gradually. Because water is retained long in the preparation, the dermal irritation level is low.

What is claimed is:

1. A hydrogel consisting essentially of water, protirelin, polyvinyl alcohol and at least one substance which can absorb 50 to 2000 times their weights of water, the substance which can absorb water being selected from the group consisting of water-absorbent resins, polyacrylate salt polymers, hyaluronic acid or a salt thereof and $\beta$-1,3-glucan.

2. The hydrogel of claim 1 wherein the polyvinyl alcohol has an average degree of polymerization in the range of 1700 to 2500.

3. The hydrogel of claim 1 wherein the polyvinyl alcohol has a saponification degree of not less than 95 mole percent.

4. The hydrogel of claim 1 wherein the total content of the at least one substance which can absorb water is within the range of 0.1 to 10 weight % based on the weight of the hydrogel.

5. The hydrogel of claim 1 wherein the water-absorbent resin is at least one resin selected from the group consisting of a metal salt of hydrolyzed copolymer composed of vinyl acetate and alkyl (meth)acrylate, crosslinked vinyl alcohol-maleic anhydride copolymer, crosslinked vinyl alcohol-acrylic acid-maleic anhydride copolymer, crosslinked isobutylene-maleic acid copolymer, saponified polyacrylonitrile graft polymer and starch-acrylic acid graft polymer.

6. The hydrogel of claim 1 wherein the water-absorbent resin is a sodium salt of a hydrolyzed copolymer composed of vinyl acetate and methyl acrylate.

7. The hydrogel of claim 1 which contains sodium hyaluronate.

8. The hydrogel of claim 1 which contains $\beta$-1,3-glucan.

* * * * *